Figure 1:

United States Patent [19]

Lange et al.

[11] 4,061,468

[45] Dec. 6, 1977

[54] STABLE TEST STRIPS HAVING A WATER-SOLUBLE PAPER LAYER AND METHODS FOR MAKING SAME

[75] Inventors: Hans Lange, Lampertheim; Walter Rittersdorf; Hans-Georg Rey, both of Mannheim-Waldhof; Wolfgang Werner, Mannheim-Vogelstang; Peter Rieckmann, Mannheim-Waldhof, all of Germany

[73] Assignee: Boehringer Mannheim GmbH, Mannheim-Waldhof, Germany

[21] Appl. No.: 592,295

[22] Filed: July 1, 1975

[30] Foreign Application Priority Data

July 30, 1974 Germany .............................. 2436598

[51] Int. Cl.² ...................... G01N 31/22; G01N 33/16
[52] U.S. Cl. .............................. 23/253 TP; 23/230 B; 427/209; 428/535; 162/140
[58] Field of Search ...................... 23/253 TP, 230 B; 162/140; 106/93; 428/212, 535; 427/209

[56] References Cited

U.S. PATENT DOCUMENTS

| | | | |
|---|---|---|---|
| 3,034,922 | 5/1962 | Böe | 162/140 X |
| 3,232,710 | 2/1966 | Rieckmann et al. | 23/253 TP |
| 3,293,683 | 12/1966 | Wyant | 428/535 X |
| 3,511,608 | 5/1970 | Anderson | 23/253 TP |
| 3,526,480 | 9/1970 | Findl et al. | 23/253 TP |
| 3,552,925 | 1/1971 | Fetter | 23/253 TP X |
| 3,975,162 | 8/1976 | Renn | 23/253 TP |

*Primary Examiner*—Norman Yudkoff
*Assistant Examiner*—Barry I. Hollander
*Attorney, Agent, or Firm*—Burgess, Dinklage & Sprung

[57] ABSTRACT

Stable test strips for the detection of components in liquids, for example blood, ketone bodies and nitrates in urine, includes two indicator layers one of which is a water-soluble paper.

13 Claims, 2 Drawing Figures

STABLE TEST STRIPS HAVING A WATER-SOLUBLE PAPER LAYER AND METHODS FOR MAKING SAME

BACKGROUND

This invention relates to stable test strips for the detection of components in liquids.

Recently, test strips have been used to a considerable extent in analysis, especially in clinical chemistry. These are pieces of absorbent material impregnated with the reagents needed for a detection reaction and upon which, shortly after moistening with the fluid to be investigated, the detection reaction takes place. A large number of such rapid tests are known, some of which are commercially available.

An important quality characteristic of rapid test strips is stability, even under extreme storage conditions such as prevail, for example, in the tropics. However, there are a number of highly sensitive rapid test strips which, unfortunately, do not possess this property to a sufficient extent. These include, for example, rapid tests for the detection of blood or hemoglobin and of ketone bodies in the urine.

The rapid test for the detection of blood must contain an organic or inorganic hydroperoxide as oxidation agent, in addition to an oxidation indicator, for example, o-tolidine. The reaction of these two components, which is catalysed by blood in the aqueous phase, cannot be fully prevented on the test strip.

In the case of the rapid test for the detection of ketone bodies, use is made of sodium nitroprusside, together with a strongly alkaline buffer. On the one hand, the detection of ketones only takes place in strongly alkaline solution but, on the other hand, sodium nitroprusside is rapidly decomposed by alkalis.

In order to overcome these difficulties, a large variety of measures have been employed, for example, separate impregnations, micro-encapsulation or dilution with film formers, swelling agents or other separating substances. In some cases, these measures result in a considerable improvement of the stability but, for extreme requirements, they are usually ineffective.

Another means for stabilization is the strict spatial separation of the incompatible reagents. Thus, for example, U.S. Pat. No. 3,511,608 describes rapid tests in which incompatible reagents are impregnated on separate papers. The papers are then fastened together, possible with the insertion of an impermeable separating layer which must be removed prior to use. These rapid tests give satisfactory results when the fluid to be investigated penetrates from above and the upper paper can be removed for the assessment of the reaction color of the lower paper.

However, in the case of commercially available rapid test strips, a form has established itself in which the test paper is wholly immersed in the fluid to be investigated, for example urine, or is even held in a stream of urine and thereafter, without additional manipulation, is compared with comparison colors.

For this purpose, usually small pieces of test paper are applied singly or in groups on to a strip-shaped holder. However, in the case of this type of construction, the measures described in U.S. Pat. No. 3,511,608 do not give a rapid test of sufficient sensitivity. There are two reasons for this: in the first place, both test papers are moistened almost simultaneously since at least the cut edges of the relatively small areas are not covered. The reagents must, therefore diffuse to one another, which takes some time, this time being especially long when one of the reagents is sparingly soluble. On the other hand, the main amount of the reaction color develops between the two papers and is thus not readily visible. For the improvement of the visibility, the upper paper can certainly be of very thin quality but, in this case, the reagent take-up capacity is very limited and considerable difficulties arise in working up due to the low mechanical stability of the thin paper.

SUMMARY

The present invention provides a stable test strip for the detection of components in liquids which does not suffer from the above-mentioned disadvantages.

According to the present invention, there is provided a stable test strip for the detection of the components in liquids, comprising two indicator layers, one of which is a water-soluble paper. By using a water-soluble paper for one of the indicator layers, a more rapid material exchange takes place and, at the same time, a readily visible color development is ensured.

DESCRIPTION

In principle, as components of water-soluble papers, all materials are suitable which combine a fibrous structure with rapid swellability. These water-soluble papers break down almost completely in water, with considerable swelling, and thereby become more or less transparent, depending upon the foreign fiber content thereof. Such papers are produced, for example, according to Published German application No. 2,042,781 or British Pat. No. 1,071,706 from carboxymethyl cellulose alone or in admixture with other fibers in an amount of up to 30% by weight. The carboxymethyl cellulose is, after the paper sheet formation, converted into its water-swellable alkali metal salts by wetting with an aqueous solution of an alkali, followed by drying. Other water-soluble papers consist, for example of methyl cellulose fibers with a methoxy content of 5-15% (see Russian Pat. Nos. 324,329 and 324,330). If residues of alkali adhere to the water-soluble papers from the production thereof, then they can be neutralized with volatile organic acids without the swellability being influenced.

The water-soluble papers can have a weight per unit area of, for example 10 to 100 $g/m^2$ and preferably of 25 to 60 $g/m^2$.

For the other reagent paper, there can be used almost any filter paper or fiber fleece, provided that it has a reasonably loose structure in order that the diffusion of the reagents is not strongly impeded.

In general, the amounts of the reagents on the two papers can be similar to those used in the known test papers but sometimes it is recommended to use somewhat larger amounts.

The rapid test strips according to the present invention can be produced, for example, in the following way:

The reagent, the stability of which is endangered, can be impregnated from an organic solvent onto the water-soluble paper, optionally together with other stability-neutral or stability-increasing additives. The other reagents are impregnated, for example, onto ordinary filter paper or fiber fleece. The dividing of the reagents can, of course, take place the other way round, the important feature being the spatial separation of the incompatible reagents. However, it is preferable to localize the components which are important for the color reaction in the soluble paper. Both impregnated papers are now laid on top of one another, the water-soluble paper being uppermost, and both papers are sealed together, preferably between a synthetic resin film and a fine meshwork in the manner described in German Pat. No. 2,118,455. The lower paper can also be stuck onto a synthetic resin strip and the water-soluble paper attached thereto by means of a water-soluble adhesive or of an adhesive screen. However, in the case of test strips of this type, there is a danger that the soluble paper might be wiped or washed off after moistening, for example when used in a stream of urine.

The test strip according to the present invention for the detection of blood in urine is produced with the use of the conventional reagents. Advantageously, in analogy with German Pat. No. 2,235,127 and Published German application No. 2,235,152, the following procedure can be employed: a filter paper or a fiber fleece is impregnated with a solution which contains a solid organic hydroperoxide, a phosphoric acid triamide, a benzoquinoline, a buffer and a long-chain organic sulphonate. A water-soluble paper is impregnated with a methanolic solution of o-tolidine or of one of its salts and of a phosphoric acid triamide. Both papers are sealed together between a synthetic resin film and a fine meshed material. The test strip produced in this manner reacts, upon dipping into urine, in practically the same manner as a strip in which all the reagents have been impregnated on one paper but, in contradistinction thereto, is of almost unlimited stability.

The test strip according to the present invention for the detection of ketone bodies in urine is produced with the use of the conventional reagents. It is advantageous to proceed analogously to Published German application No. 1,256,920: filter paper or fiber fleece is impregnated with a solution of phosphate buffer and glycine. The water-soluble paper is impregnated with a methanolic solution of sodium nitroprusside and the two papers are then sealed in the manner described above.

The test strip according to the present invention for the detection of nitrate in urine is also produced with the use of conventional reagents. Advantageously, over a filter paper coated with zinc dust there can be sealed a soluble paper which is impregnated with nitrite detection reagents according to German Pat. No. 1,941,370. A rapid test strip of this type cannot be produced on one of the previously employed test papers since zinc is not stable in the presence of the acidic nitrite reagent.

Figure 2:

Embodiments of the test strips of the invention are illustrated in the accompanying drawings in which FIG. 1 represents a test strip wherein the layer assembly is held together and to the plastic film holding strip by means of a covering comprising a net or fine meshed material;

FIG. 2 is an embodiment wherein the two layers of the inventive test strips are held together by means of an adhesive and the entire test strip assembly is adhered to the plastic film holding strip by another adhesive layer as shown therein.

The following Examples are given for the purpose of illustrating the present invention:

EXAMPLE 1

Blood Test
Test Paper A

Filter paper (2316 of Schleicher & Schull) is impregnated with a solution of the following composition and subsequently dried:

| | |
|---|---|
| 1.2 molar citrate buffer, pH 5.25 | 25 ml. |
| ethylenediamine-tetraacetic acid, disodium salt | 0.5 g. |
| 2,5-dimethylhexane-2,5-dihydroperoxide (approx. 80%) | 1.6 g. |
| phenanthridine | 1.0 g. |
| phosphoric acid trimorpholide | 12.7 g. |
| dioctyl sodium sulphosuccinate | 1.0 g. |
| methanol | 35.0 ml. |
| distilled water | ad 100.0 ml. |

Test Paper B

A water-soluble paper of 90% by weight carboxymethyl cellulose and 10% by weight cellulose (weight per surface area 30 g/m²) is impregnated with a solution of the following composition and subsequently dried:

| | |
|---|---|
| o-tolidine | 1.0 g. |
| phosphoric acid trimorpholide | 3.0 g. |
| glacial acetic acid | 8.0 g. |
| distilled water | 10.0 ml. |
| methanol | ad 100.0 ml. |

Test papers A and B are cut up into 6 mm. wide strips and, with B over A, sealed in between bands of polyethylene-laminated polyester film and fine-mesh nylon net. The bands are cut transversely into 6 mm. wide strips: in this manner, test strips are obtained which, close to the lower end, carry the quadratic reactive region under the mesh.

When these test strips are dipped into blood-containing urine, then, depending upon the blood concentration, more or less strong blue-green colorations are obtained. The detection sensitivity is about the same as a single test paper which is produced from Test Paper A by impregnation with a solution of 0.2 g. o-tolidine in 100 ml. toluene and subsequent drying. However, whereas this latter test paper loses a considerable amount of sensitivity after storage for about half a year, the reactivity of the test strip according to the present invention is practically unchanged.

EXAMPLE 2

Ketone test
Test Paper A

A cellulose-polyamide mixed fleece is impregnated with a solution of the following composition and subsequently dried:

| | |
|---|---|
| trisodium phosphate dodecahydrate | 21.0 g. |
| disodium hydrogen phosphate | 9.0 g. |
| glycine | 18.7 g. |
| distilled water | 100.0 ml. |

Test Paper B

A soluble paper of 100% carboxmethyl cellulose with a surface weight of 60 g/m² is first impregnated with a solution of 5% each glacial acetic acid and water in methanol and then dried. Thereafter, it is further impregnated with a 3% methanolic solution of sodium nitroprusside and again dried.

Test papers A and B are cut up into 6 mm. wide strips and, with B over A, sealed in, in the manner described in Example 1.

The test strips obtained react with acetoacetate-containing urine with a violet color and retain their reactivity even after being subjected to a temperature of 60° C for a week.

A single test paper, which has been produced by the post-impregnation of test paper A with a 1% methanolic solution of sodium nitroprusside is, after this heat treatment, almost completely destroyed.

EXAMPLE 3

Nitrate Test
Test Paper A

Filter paper is thinly painted with a slurry of zinc dust and a 1% methanolic solution of polyvinylpyrrolidone and subsequently dried.

Test Paper B

A soluble paper of 100% carboxymethyl-cellulose with a surface weight of 60 g/m$^2$ is impregnated with a solution of the following composition and subsequently dried:

| | |
|---|---|
| sulphanilamide | 0.17 g. |
| 3-hydroxy-1,2,3,4-tetrahydrobenzo(h)-quinoline | 0.98 g. |
| tartaric acid | 2.5 g. |
| glacial acetic acid | 8 ml. |
| water | 20 ml. |
| methanol | ad 100 ml. |

Test papers A and B are cut up into 6 mm. wide strips and, with B over A, sealed in in the manner described in Example 1.

The test strips thus obtained react with nitrate-containing liquids with a red color, even after storage for 3 days at a temperature of 60° C.

In the case of a single test paper, the metallic zinc is destroyed in a short time by the acid, the test paper thereby becoming useless.

What is claimed is:

1. Stable test strip for the detection of a component in an aqueous liquid comprising two indicator layers containing at least one reagent in each layer, said reagents forming, upon contact with the liquid containing said component, a color detectable throughout said strip, wherein one of said indicator layers is a water soluble paper.

2. Test strip of claim 1 wherein the water-soluble paper comprises fibers selected from the group consisting of methyl cellulose and an alkali metal salt of carboxymethyl cellulose.

3. Test strip of claim 2 wherein the water-soluble paper contains additional fibers.

4. Test strip of claim 3 wherein the additional fibers are cellulose fibers.

5. Test strip of claim 1 wherein the water-soluble paper has a surface weight of 10-100 g/m$^2$.

6. Test strip of claim 5 wherein the water-soluble paper has a surface weight of 25-60 g/m$^2$.

7. Test strip of claim 1 wherein the other indicator layer is a water-insoluble layer selected from the group consisting of absorbent paper and fleece.

8. Stable test strip for the detection of blood in urine comprising two indicator layers which are each impregnated with reagents for the detection of blood, said reagents forming upon contact with said blood-containing urine, a color detectable throughout said strip, one of said indicator layers being a water-soluble paper.

9. Stable test strip for the detection of ketone bodies in urine comprising two indicator layers which are each impregnated with reagents for the detection of ketone bodies, said reagents forming upon contact with the ketone body-containing urine, a color detectable throughout said strip, one of said indicator layers being a water-soluble paper.

10. Stable test strip for the detection of nitrate in urine comprising two indicator layers which are each impregnated with reagents for the detection of nitrate, said reagents forming upon contact with said nitrate-containing urine, a color detectable throughout said strip, one of said indicator layers being a water soluble paper.

11. Test strip of claim 1 wherein the two indicator layers are placed on top of one another and sealed between a synthetic resin film and a fine meshed material.

12. Test strip of claim 1 wherein the non-water-soluble indicator layer is adhered to a synthetic resin strip and the water-soluble paper is attached thereto.

13. Process for the production of stable test strips for the detection of component materials in an aqueous liquid, which comprises impregnating two indicator layers individually, each with at least one detection reagent, one of said indicator layers being a water-soluble paper, drying said layers and uniting same to form said test strip.

* * * * *